(12) United States Patent
Hagl (10) Patent No.: US 9,739,665 B2
(45) Date of Patent: Aug. 22, 2017

(54) COVERING CAP AND MEASURING DEVICE

(71) Applicant: Peter Hagl, Vienna (AT)

(72) Inventor: Peter Hagl, Vienna (AT)

(73) Assignee: Vasema Diagnostics AG, Zurich (CH)

( * ) Notice: Subject to any disclaimer, the term of this patent is extended or adjusted under 35 U.S.C. 154(b) by 9 days.

(21) Appl. No.: 14/406,274

(22) PCT Filed: May 24, 2013

(86) PCT No.: PCT/AT2013/050112
§ 371 (c)(1),
(2) Date: Dec. 8, 2014

(87) PCT Pub. No.: WO2013/181681
PCT Pub. Date: Dec. 12, 2013

(65) Prior Publication Data
US 2015/0126827 A1 May 7, 2015

(30) Foreign Application Priority Data
Jun. 8, 2012 (AT) ...................................... 662/2012

(51) Int. Cl.
*A61B 19/02* (2006.01)
*B23K 26/38* (2014.01)
(Continued)

(52) U.S. Cl.
CPC .......... *G01J 5/021* (2013.01); *A61B 1/00142* (2013.01); *A61B 5/145* (2013.01); *A61B 5/14546* (2013.01); *A61B 5/441* (2013.01); *A61B 5/443* (2013.01); *B29C 51/087* (2013.01); *A61B 2560/0431* (2013.01); *A61B 2562/247* (2013.01); *B29C 51/08* (2013.01);
(Continued)

(58) Field of Classification Search
CPC ............. Y10T 428/13; Y10T 428/1372; Y10T 428/1397; A61B 19/02; A61B 50/00; A61B 90/40; A61B 5/145; A61B 5/14546; A61B 5/441; A61B 5/443; A61B 2050/0068; A61B 2050/0078; A61B 2560/0431; A61B 2562/247; A61B 1/00142; G01J 5/021
See application file for complete search history.

(56) References Cited

U.S. PATENT DOCUMENTS 4,207,160 A 6/1980 Frankenberger et al.
4,303,076 A 12/1981 Danek
(Continued)

FOREIGN PATENT DOCUMENTS

DE 19604200 A1 8/1997
EP 0928969 A2 7/1999
(Continued)

*Primary Examiner* — Andrew Perreault
(74) *Attorney, Agent, or Firm* — Laurence A. Greenberg; Werner H. Stemer; Ralph E. Locher (57) ABSTRACT

A covering cap, in particular for placing on a skin analyzer, contains an end wall bounded by a circumferential edge, and a circumferential wall adjoining the circumferential edge of the end wall. At least one part of the covering cap has a thickness that is less than a thickness of the circumferential wall in a portion of the circumferential wall that lies in the region or end of the circumferential wall remote from the end wall. The end wall is of a gas-permeable configuration.

7 Claims, 8 Drawing Sheets (51) Int. Cl.
　　　*G01J 5/02*　　　(2006.01)
　　　*A61B 1/00*　　　(2006.01)
　　　*A61B 5/145*　　 (2006.01)
　　　*A61B 5/00*　　　(2006.01)
　　　*B29C 51/08*　　 (2006.01)
　　　*B29K 67/00*　　 (2006.01)
　　　*B29K 105/00*　　(2006.01)

(52) U.S. Cl.
　　　CPC .. *B29K 2067/003* (2013.01); *B29K 2105/256* (2013.01); *Y10T 428/13* (2015.01); *Y10T 428/1372* (2015.01); *Y10T 428/1397* (2015.01)

(56) References Cited

U.S. PATENT DOCUMENTS

| | | |
|---|---|---|
| 5,088,834 A | 2/1992 | Howe et al. |
| 6,099,802 A | 8/2000 | Pugh |
| 6,156,148 A | 12/2000 | Beerwerth et al. |
| 6,612,735 B2 | 9/2003 | Tomioka et al. |
| 7,237,949 B2 * | 7/2007 | Lantz .................. G01J 5/0003 374/158 |
| 2001/0034479 A1 | 10/2001 | Ring et al. |
| 2007/0058692 A1 | 3/2007 | Huang et al. |
| 2010/0329951 A1 | 12/2010 | Jung et al. |
| 2011/0202121 A1 | 8/2011 | Wen |
| 2012/0027047 A1 | 2/2012 | Lane et al. |

FOREIGN PATENT DOCUMENTS

| | | |
|---|---|---|
| EP | 1262753 A1 | 12/2002 |
| WO | 2004103431 A2 | 12/2004 |

* cited by examiner

COVERING CAP AND MEASURING DEVICE

The invention concerns a cap, in particular to be placed on a skin analysis device. The invention further concerns a measuring device, in particular for skin analysis. Moreover, the invention concerns a method for producing a cap.

BACKGROUND OF THE INVENTION

Field of the Invention

The background of the invention is the use of caps, also known as 'hygienic caps', to cover sensors of a measuring device. Caps are necessary for the clean—sterile or non-sterile—measurement of persons, animals, or materials without contaminating the sensor or measuring device covered by the cap. Such caps are used in the prior art, e.g., in an infrared thermometer, whereby the infrared sensor is covered to protect it from contamination. The use of caps serves to avoid transmitting diseases to other persons or parts of the body.

However, caps available from the prior art have numerous disadvantages. On the one hand, there is the problem that prior-art caps require substantial space and are difficult to fold. Additionally, there is the problem of the hygienic handling of caps and obtaining an optimal fit, in particular tensioning the cap in order to allow the sensitive part of a measuring device. There is also the problem of disposing of a cap without touching it.

It is known from the prior art that hygienic caps are made of the most even material with the most even possible thickness, preferably polyethylene or polypropylene, whereby the area of the surface of the respective cap is thinned by means of a microtone meter or laser in the frontal wall area, which is penetrated by the infrared beam characterising the respective temperature.

Additionally, the surface in the area of the frontal wall may also be thinned by extruding a melt with subsequent insertion of a film. The caps obtained in this manner are quite stiff, which makes it difficult, on the one hand, to tighten the caps around the measuring device, whilst making it impossible to save space when recycling by folding or compressing it onto a flat object.

BRIEF SUMMARY OF THE INVENTION

Thus, the objective of the invention is to provide a cap that advantageously covers the measuring device and optimally adapts to the shape of the measuring device, and that allows for easy, low-volume disposal.

Another objective of the invention is to provide an advantageous method for producing a cap.

Furthermore, the invention seeks to provide a measuring device allowing for advantageous, no-touch disposal with a cap according to the invention.

According to the invention, in a cap, in particular for placement on a skin analysis device, comprising a lateral wall delimited by a circumferential edge, as well as a jacket wall attached to the circumferential edge of the front wall, it is provided for the front wall to be gas-permeable.

A particular further development of the invention provides for the jacket wall to have at least one circumferential section, the thickness of which is less than the thickness of the jacket wall in the section of the end of the jacket wall facing away from the front wall. This measure provides a certain degree of flexibility in the area of the circumferential section, allowing for optimal adaptation of the cap to the respective measuring device.

Generally, in any type of cap, in particular all aforementioned further developments of the invention, it is advantageous for the front wall to have a thickness, at least in one place, of less than 100 µm, preferably between 0.1 µm and 20 µm, in particular between 5 µm and 10 µm. This makes it possible to provide a front wall through which gases may diffuse and a cap is possible to protect the sensor from harmful substances without compromising the overall functionality of the measuring device, because the configuration of the front wall allows the substances being measured to diffuse through that wall.

In particular, it may be provided for the front wall to have, in particular, a constant thickness. This allows for particularly exact measurements.

To increase the stability and resistance of the cap, it may be provided for a base wall continuing the jacket wall on the end facing away from the front wall, in particular in a single piece, and preferably runs outward from the jacket wall parallel or at an angle of no more than 10° to the front wall, whereby the base wall is preferably radial in shape and has, in particular, an outer radius between 2 mm and 50 mm and/or an inner radius between 1 mm and 45 mm, and/or a width of 0.5-35 mm.

A particularly advantageous adaptation to measuring devices with an ejection device or element provides that the jacket wall in the area of the circumferential edge of the front wall protrudes outward at an angle of 20°-95°, in particular 60°-80° to the front wall, whereby the jacket wall expands, in particular conically.

An advantageous aspect for the connection of the cap to a measuring device provides for the cap has locking recesses and/or locking protrusions on the end of the jacket wall facing away from the front wall for removable attachment to a measuring device, and/or in particular the individual locking recesses and/or protrusions each have the same normal distance from the front wall and/or are distributed evenly in the circumferential direction of the jacket wall, and/or whereby the total number of locking recesses and/or protrusions is two or four, and/or in particular the locking recesses and/or protrusions to protrude away from the jacket wall at an angle of 5°-40° and/or no more than 2 mm, in particular no more than 0.3 mm or penetrate into it. This additionally allows the cap to be simply and automatically removed from the measuring device.

Another preferred aspect of the invention provides for the front wall to be penetrable by radiation, vapour, moisture, particles, and/or light, and/or to have a number of—in particular vapour- or gas-permeable—microholes. This allows the cap thus formed to be used in numerous different measuring devices.

A particularly adaptable, robust, and resistant further development of the invention provides for the cap to be produced of coordinated materials and/or in one piece, in particular of a thermoplastic or plastically deformed or deformable polymer, preferably one of the following materials or a mixture thereof:

PETG (Polyethylene terephthalate Glycol),
PP (Polypropylene),
PE (Polyethylene),
PC (Polycarbonate),
PVC (Polyvinyl chloride),
PS (Polystyrene),
ABS (Acrylonitrile butadiene styrene),
HDPE (High Density Polyethylene), LDPE (Low Density Polyethylene),
PET (Polyethylene terephthalate),
PMMA (Polymethyl methacrylate),
ECOTERM S 900 T1,
PETG/Copolyester 67639,
whereby the material of the cap (10), in particularly additionally, contains one or more of the following components:
Additives,
Stabilisers
Colourants
Fillers
Reinforcing materials
whereby, in particular, the material of the cap has a colourant and the front wall is configured so as to be opaque or absorbent to certain, in particular visible, wavelengths.

A cap that is particularly easy to produce and allows for simple folding or collapsing provides for the thickness of the jacket wall to increase from the front wall to the end of the jacket wall that is farthest from the front wall, in particular over part of the jacket wall, and preferably continuously.

A cap that is particularly robust in the area of the front wall, allowing easy handling during placement on the measuring device, provides for the jacket wall to have a first thickening section near the front wall, in particular following from the circumferential edge, in which the thickness of the jacket wall exceeds the thickness of the front wall, for the jacket wall to have an intermediate section following from the first thickening section, whereby the thickness of the jacket wall in the intermediate section is less than the thickness of the jacket wall in the first thickening section, for the jacket wall to have a second thickening section following from the intermediate section and extending until the end of the jacket wall that is farthest from the front wall, and for the thickness of the jacket wall to be greater in the second thickening section than the thickness of the jacket wall in the intermediate section.

Simple production is made possible by the fact that the thickness of the jacket wall, in particular in the axial or radial direction, has a course that is continuous over the jacket wall and free of kinks or edges, and/or its thickness is considered to be the respective average thickness in the respective section of the jacket wall, and/or that the jacket wall, in particular with the exception of the area of the locking protrusions and/or recesses, to be rotationally symmetric.

Particularly advantageous configurations and further developments of the invention provide for the thicknesses of the first thickening section, the intermediate section, and the second thickening section to have the following ratio:
$2 < d_1 : d_2 < 5$ and/or $2 < d_3 : d_2 < 5$ and/or $0.8 < d_1 : d_3 < 1.25$
and/or for the thicknesses of the first thickening section, the intermediate section, and the second thickening section to be set as follows:
150 μm$< d_1 <$250 μm and/or 50 μm$< d_2 <$100 μm and/or 150 μm$< d_3 <$250 μm. This results in a particularly advantageous cap that is particularly stable and robust in its terminal area farthest from the front surface, has increased stability in the area of the front surface, and has good elasticity and compressibility in the intermediate area between the two thickening areas.

A particularly advantageous selection of the individual heights of the thickening sections, as well as the intermediate section, provides for the following ratio between the height of the first thickening section, the height of the intermediate section, and the height of the second thickening section:
$0.2 < h_1 : h_2 < 0.6$ and/or $0.8 < h_3 : h_2 < 1.25$ and/or $0.2 < h_1 : h_3 < 0.6$.

To cover typical measuring devices, it is advantageous in many cases for the jacket wall to have a height of 2 mm-80 mm, and/or for the ratio between the height and the maximum dimension, in particular the diameter or diagonal, of the front wall (1) to be between 0.01 and 55.

In order to allow for particularly gentle measuring of the object or person being measured, it may be provided for the front wall to be circular, and in particular to be 1-50 mm in diameter, or for the front wall to be square or rectangular and whereby the lateral edges of the front wall are between 2 and 40 mm in length.

Additionally, the invention concerns a measuring device, in particular for skin analysis, which can be covered with a cap having locking recesses and/or protrusions. In particular, the measuring device can be covered with a cap according to the invention and locked together with it. The measuring device comprises a housing and a sensor contained therein, whereby the housing has a conically tapering component with a front surface, on which a number of locking recesses and/or protrusions is provided to lock together with the locking recesses and/or protrusions of the cap, in particular such that, when locked, the front wall abuts the front surface of the cap. With this measuring device, it is quite easy to dispose of caps hygienically and simply by throwing or shooting the cap into a dedicated container. In particular, it is not necessary to touch the cap in the area that was in contact with the object or life form to be measured during the measurement.

According to an advantageously structured configuration for the ejection of the cap, an ejection element is provided that is arranged in the end of the housing component that is farthest from the front wall, and that is farther away from the front wall than the locking recesses and/or protrusions, whereby the ejection element is configured to push a locked cap by applying pressure to the cap in the direction of the front wall, and/or whereby the ejection element is mounted on the housing so as to be movable in the direction of the front wall.

In order to obtain a defined ejection and disposal of the cap with the measuring device, it may be provided for a lever extension to be attached to the ejection element or to depart from the ejection element, or for the ejection element to be connected with a lever extension, whereby the lever extension is connected pivotably with the housing in its central area, resulting in a two-arm lever, on one end of which the ejection element is arranged, whereby the lever extension that hinges on the housing presses the ejection element towards the front wall when it swivels.

In order to allow for completely contact-free removal of the cap from the measuring device, it may be provided for an ejection element to be arranged in the end of the housing component that is farthest from the front wall, and that is farther away from the front wall than the locking recesses and/or protrusions, for the ejection element to be configured to push a locked cap by applying pressure to the cap in the direction of the front wall, and/or for the ejection element to be mounted on the housing so as to be movable in the direction of the front wall (22). This allows the cap to be removed from the measuring device with no hand contact at all; rather, it can be removed by actuating the ejection element.

The ejection can be particularly simple if the ejection element is annular, in particular radially cylindrical and surrounds the conically tapering housing component.

A particularly advantageous actuation of the ejection element provides for a lever extension to be attached to the ejection element or to depart from the ejection element, or for the ejection element to be connected with a lever extension, whereby the lever extension is connected pivotably with the housing in its central area, resulting in a two-arm lever, on one end of which the ejection element is arranged, whereby an actuator is provided, in particular on its other end, whereby the lever extension that hinges on the housing, in particular by applying force to the actuator, presses the ejection element towards the front wall when it swivels.

To further improve operability and usability, it may be provided for the ejection element and/or lever extension to be subjected to a force or bias that pushes or pulls the ejection element away from the front wall by a spring element.

For particularly simple and effective ejection of the cap, it is provided for the individual locking recesses and/or protrusions each to have the same normal distance from the front wall and/or be distributed evenly in the circumferential direction of the jacket wall, and/or for the total number of locking recesses and/or protrusions to be two or four, and/or for the locking recesses and/or protrusions to protrude away from the jacket wall at an angle of 10°-30° and/or no more than 1 mm, in particular no more than 0.5, and/or that two locking recesses and/or protrusions are provided at the same distance from a point in the area in which the lever extension is connected to the ejection element or departs from it.

A cap with a particularly thin front wall may be produced by the method according to the invention. In this regard, it is provided that: a) a polymer film, in particular a film consisting of PETG (polyethylene terephthalate glycol) is used as the raw material for a deep-drawing process, preferably having a thickness between 0.04 and 0.5 mm, b) a stamp with a number of separately movable substamps that abut one another is pressed on the polymer film, whereby the individual substamps are moved normally to the level of the polymer film, and whereby the polymer film (31) is pressed into a countermould by the pressure of the substamps and deformed into a cap shape, c) the individual substamps of the stamp are spaced apart from one another during or after step b), whereby each of the substamps is moved radially outward from the position of the stamp, thus forming a front wall in the polymer film, in particular having a thickness of less than 100 µm, preferably between 3 µm and 20 µm, in particular between 5 µm and 10 µm.

The invention uses a variation of a deep-drawing method in order to obtain particularly thin wall thicknesses of the front wall. In particular the rotary component of the moulding of the caps allows for the formation of very thin walls.

To form caps with different jacket wall thicknesses, it may be provided that, following step c), the substamps fare removed from the cap shape formed, and another stamp with an even front surface and an expanding stamp body is inserted into the volume formed in the polymer film by the substamps, whereby the polymer film is brought into a cap shape between the additional stamp and a second countermould, whereby preferably the polymer film, the additional stamp, or the second countermould is advanced after heating the polymer film to a temperature between 50 and 90° C.

In order to obtain different wall thicknesses, it may be provided that, to set the respective thickness of the jacket wall originating from the front wall, the feed speed and/or temperature of the substamps, the additional stamp, and/or the temperature of the polymer film and/or the temperature of the first and second countermould is set, whereby, to reduce the wall thickness in the marginal area of the recess formed by the additional stamp, the aforementioned temperatures and the feed speed are increased, and whereby, to increase the wall thickness in the marginal area of the recess formed by the additional stamp, the aforementioned temperatures and the feed speed are reduced.

A particularly advantageous cap, which can be collapsed after use and advantageously removed from a measuring device, may be produced by setting the temperature of the additional stamp and/or the polymer film and the feed speed of the additional stamp such that during a first feed period of the additional stamp, a section of the jacket wall is formed with a specified thickness, in particular 50-100 µm, and during a second feed period, following the first feed period, of the additional stamp, a section of the jacket wall is formed with a specified thickness, in particular 150-250 µm, that is thicker than the thickness of the jacket wall formed in the first feed period.

Advantageously, it can be provided that the wall thickness is set during the first feed period of the additional stamp to a value corresponding to between double and five times the wall thickness of the jacket area formed during the moulding of the front wall by the insertion of the substamps.

To produce caps with circular front walls, it may be provided that the substamps are rotated spirally outward along an outward expanding curve during their movement away from their centre in step c).

A particularly adaptable, robust, and resistant further development of the invention provides for the polymer film to consist of a thermoplastic or plastically deformed or deformable polymer, preferably one of the following materials or a mixture thereof:

PETG (Polyethylene terephthalate Glycol),
PP (Polypropylene),
PE (Polyethylene),
PC (Polycarbonate),
PVC (Polyvinyl chloride),
PS (Polystyrene),
ABS (Acrylonitrile butadiene styrene),
HDPE (High Density Polyethylene),
LDPE (Low Density Polyethylene),
PET (Polyethylene terephthalate),
PMMA (Polymethyl methacrylate),
ECOTERM S 900 T1,
PETG/Copolyester 67639,
whereby the material of the cap, in particular additionally, contains one or more of the following components:
Additives,
Stabilisers
Colourants
Fillers
Reinforcing materials whereby, in particular, the material of the cap has a colourant and the front wall is configured so as to be opaque or absorbent to certain wavelengths.

To form characteristics, in particular locking recesses, in the inner area of the lateral surface and the front surface, it may be provided that, after partial or complete moulding of the jacket wall, the substamps or the additional stamp is retracted, and the moulded volume is subjected to compressed air—in particular hated compressed air—and, if applicable, is then inserted into the moulded volume to carry out the next moulding step. whereby locking recesses are formed in the inner lining of the jacket wall, in particular by applying compressed air.

In order to remove the caps produced from the body of the polymer film, it may be provided that, after the moulding of the jacket wall, the remaining polymer film bordering on the jacket wall is separated along a cutting line that is selected, in particular, such that a part of the excess polymer film remaining on the jacket wall is within the cutting line and forms a base wall.

In order to determine the permeability of the film, it may be provided for the polymer film, in particular after moulding, to be heated for a specified period, in particular at least 3 s, to a specified temperature between 30 and 120° C., in particular between 50 and 90° C., and/or for the substamps and/or the additional stamp and/or the countermoulds used to be heated before processing the polymer film to a temperature between 30 and 120° C., in particular 50 and 90° C., and are kept at such a temperature during processing.

In particular, in order to allow better diffusion of substances through the front wall, provision may be made for holes, in particular microholes or nanoholes, to be formed in the front wall by means of a laser or a heated microneedle or nanoneedle or by etching.

In order to allow for better diffusion of substances through the front wall, it may be provided for holes, in particular microholes or nanoholes, to be formed in the front wall, in particular by means of a laser or a heated microneedle or nanoneedle.

BRIEF DESCRIPTION OF THE SEVERAL VIEWS OF THE DRAWING

Several exemplary embodiments of the invention will be discussed by reference to the following drawings.

FIG. 1a shows a cross section of a first embodiment of a cap according to the invention. FIG. 1b shows a side view of the cap of FIG. 1a.

FIG. 4 shows a measuring device according to the invention with a cap on.

DESCRIPTION OF THE INVENTION

Figures 1A, 1B:
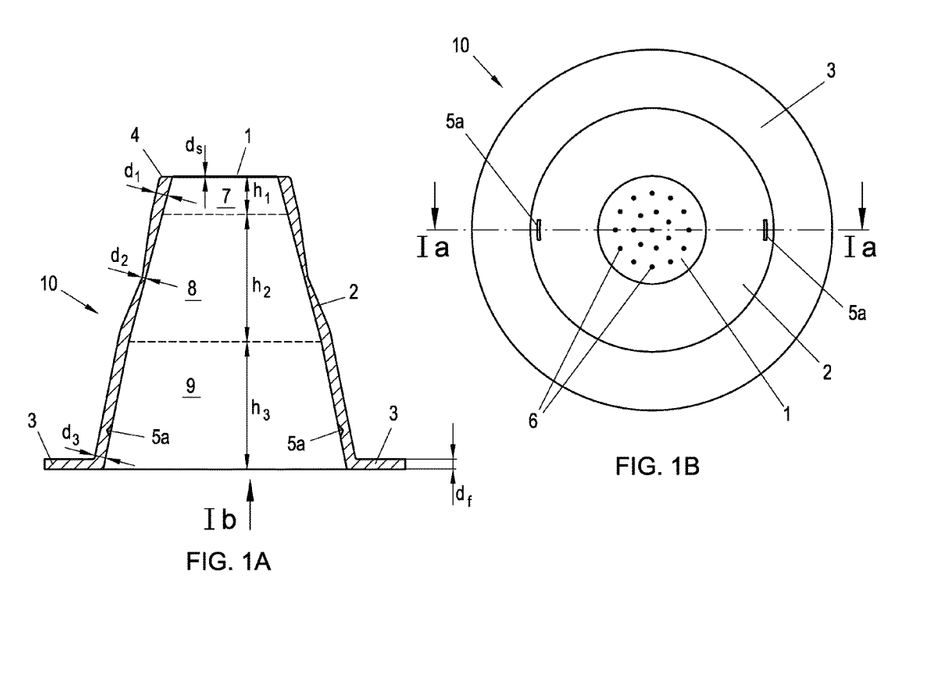

FIG. 1a shows a cross section (cutting line 1a in FIG. 1b) of a first embodiment of a cap 10 according to the invention. This cap 10 is shown from below in FIG. 1b according to the cutting line 1b indicated in FIG. 1a. This cap 10 has a circular front wall 1, delimited by a circumferential edge 4. From the circumferential edge 4 of the front wall 1 follows a jacket wall 2, the end of which that faces away from the front wall 1 is continued from a base wall 3. The jacket wall 2 is expands nearly conically in the following exemplary embodiment, and deviates outward in the area of the circumferential edge 4 from the front wall 1 at an angle α of 75°.

The front wall 1 has a very small thickness $d_S$ of 10 μm; advantageously, this wall thickness $d_S$ may be between 0.05 μm and 20 μm, in particular between 3 μm and 20 μm. The front wall 1 has a diameter of 5 mm in this case. Generally, this diameter may vary widely; in particular, diameters between 2 and 20 mm area advantageous, whereby, depending on the application, larger diameters of up to 100 mm certainly may be used.

An alternative embodiment of the invention, not shown, has a square front wall 1 with a substantially equal surface area to the exemplary embodiment shown in FIG. 1, rather than a circular front wall 1, and has an edge length of approximately 10 mm. Alternatively, the front wall 1 may also be rectangular, square, or elliptical in shape, whereby the side edges of the front wall 1 may be approximately between 2 and 40 mm long, in particular between 5 and 8 mm long.

In the exemplary embodiment shown in FIG. 1a, the jacket 2 of the cap 10 consists of three parts, and, near the front wall 1, comprises a first thickening section 7, following from the circumferential edge 4, having a thickness $d_1$; in this exemplary embodiment, a thickness $d_1$ between 150 and 250 μm was selected for the first thickening section. The thickness $d_1$ of the jacket wall 2 in the first thickening section 7 exceeds the thickness $d_S$ of the front wall, and is 5 μm-8 μm in this exemplary embodiment. The first thickening section 7 is formed circumferentially, whereby the first thickening section 7 is circularly delimited on the end farthest from the front wall 1, and whereby an intermediate section 8 follows the first thickening section 7 in this boundary area.

In the intermediate section 8, the jacket wall 2 has a thickness $d_2$, that is less than the thickness $d_1$ of the jacket wall 2 in the first thickening section 7. In this exemplary embodiment, a thickness $d_2$ of the jacket wall 2 in the intermediate section 8 of 50-150 μm was selected. The intermediate section 8 is circularly delimited at the end farthest from the first thickening section 7, whereby this circular limit is followed by a second thickening section 9, in which the thickness $d_3$ of the jacket wall 2 is greater than the thickness $d_2$ of the jacket wall 2 in the intermediate section 8. In this exemplary embodiment, a thickness $d_3$ between 150 and 250 μm was selected for the first thickening section. The second thickening section 9 here follows the end of the jacket wall 2 farthest from the front wall 1, in particular, the second thickening section 9 borders directly on the base wall 3.

This special configuration gives the jacket wall 2 a circumferential section in the form of the intermediate section 8, in which the thickness $d_2$ is less than the thickness $d_3$ of the jacket wall 2 in the area of the end of the jacket wall 2 facing away from the front wall 1. The thickness of the jacket wall 2 constantly/continuously decreases in the axial or radial direction, from the thickness $d_1$ in the first thickening area 7, reaching a minimal level in the intermediate section 8; the thickness of the jacket wall 2 then increases in the second thickening area 9 up to the end of the lateral surface farthest from the front wall 1.

The thickness of the jacket wall 2 has a continuous course free of kinks or edges over the jacket wall 2. To the extent necessary for the following observations, the thickness of the jacket wall 2 in the respective section 7, 8, 9 of the jacket wall 2 will be understood to be the average thickness in the respective section.

In order to allow for a particularly advantageous adaptation of the front wall 1 to the front surface 21 (FIG. 4) of a measuring device 20, the thickness of the jacket wall 2 in the area of the intermediate section 8 is thinner than in the other two thickening sections 7, 9. The ratio of the thickness $d_2$ in the intermediate section 8 to the thickness $d_1$ in the first thickening section 7 is approximately between 2 and 5. The ratio of the thickness $d_2$ in the intermediate section 8 to the thickness $d_3$ in the second thickening section 9 is approximately between 2 and 5. The thickness $d_1$ of the lateral surface 2 in the first thickening section as well as the thickness $d_3$ of the lateral surface 2 in the second thickening section 9 are roughly equal. The ratio between these two thicknesses $d_1$, $d_3$ is approximately between 0.8 and 1.25.

In this exemplary embodiment, the jacket wall 2 has the following average thickness values in the individual sections 7, 8, 9:

$d_1$=0.18 mm $d_2$=0.08 mm $d_3$=0.22 mm

The height h of the jacket wall 2 is 20 mm in this exemplary embodiment, but, depending on the shape and structure of the measuring device 20 to be covered, may have different values, typically between 15 and 35 mm. The ratio between the height h of the jacket wall 2 and the maximum dimension of the front wall 1 is between 0.02 and 5.

The first thickening section 7 is formed in the area of the front wall 1, and has a height of approximately 4 mm in this exemplary embodiment. The other two sections of the jacket wall 2, i.e., the intermediate section 8 and the second thickening section 9, have approximately the same height, in this case app. 10 mm each. Typically, the height $h_1$ of the first thickening section 7, the height $h_2$ of the intermediate section 8, and the height $h_3$ of the second thickening section 9 are in the following ratio to one another:

$0.2 < h_1 : h_2 < 0.6$; $0.8 < h_3 : h_2 1.25$; $0.2 < h_1 : h_3 < 0.6$

A specific further configuration of the invention allows for improved handling and less susceptibility of the cap 20 to tears and breakage. In order to provide better handling, a reinforcing element is arranged in the cap 10 in the area of the second thickening section 9, or in its lower terminal area farthest from the front wall 1. Such a reinforcing element is connected with the inner or outer lining of the lateral surface 2, and is in the shape of a cuff, the surface of which corresponds to the surface of the inner or outer lining. This cuff preferably consists of reinforced plastic or a polymer having a greater rigidity than the polymer of which the cap 10 consists.

The base wall 3, continuing the jacket wall 2 on the end farthest from the front wall 1, runs parallel to the front wall 1 in this exemplary embodiment. Alternatively, however, the base wall 3 could run outward at an angle of 10° to, and away from, the front wall 1. Preferably, the base wall 3 deviates outward from the jacket wall 2, whereby the normal distance of the base wall 3 from the front wall increases with increasing radial distance.

The base wall 3 in this exemplary embodiment is radial in shape and parallel to the front wall 1, and has an external diameter of 21 mm and an internal diameter of 18 mm. The radial width in this case is 1.5 mm.

Figure 4:
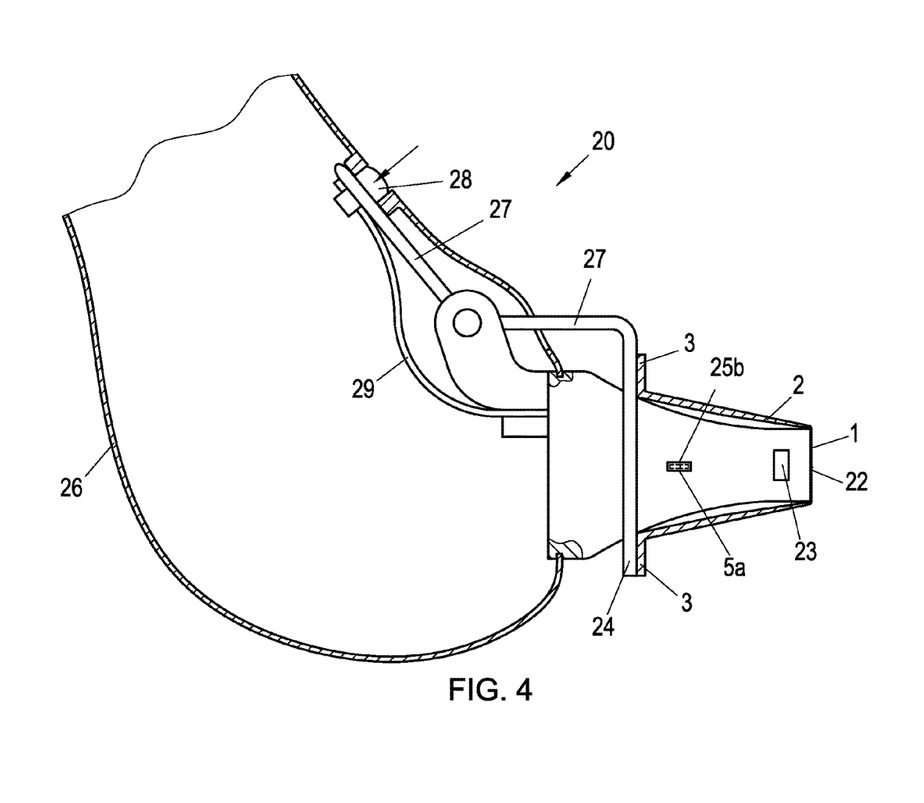

Additionally, the cap 10 has locking recesses a on the inside of the jacket wall 2, allowing for removable attachment to a measuring device 20 (FIG. 4). In this exemplary embodiment, two locking recesses 5a are arranged such that they are opposite one another on the jacket wall of the cap 10. Alternatively, instead of locking recesses 5a, locking protrusions (not shown) may be provided. Generally, the purpose of the locking recesses 5a and protrusions is to allow for locking attachment to a measuring device 20 or with locking recesses and/or protrusions 25b arranged on the measuring device.

The two locking recesses 5a are formed in this exemplary embodiment as recesses on the inside of the jacket wall 2 in the area of the second thickening section 9, and run approximately at an angle $\beta_1$, $\beta_2$ of 20° to the jacket wall 2. The locking recesses 5a protrude approximately 60 μm into the second thickening area 9.

Alternatively, it is also possible to provide locking protrusions instead of locking recesses 5a. They protrude inward away from the jacket wall 2 at an angle $\beta_1$, $\beta_2$ of 10°-30°, and deviate approximately 1.5 mm inward from the jacket wall 2. The locking protrusions 5a are opposite one another at the same height, each with the same normal distance from the front wall 1, and are distributed evenly in the circumferential direction of the jacket wall 2, i.e., they are at an angle of 180° to one another in this exemplary embodiment.

Alternatively, it is also possible for the locking recesses 5a or the locking protrusions to be present in greater numbers. In particular, a number of four locking protrusions or recesses 5a has proved advantageous; they are spaced respectively 90° from one another in the circumferential direction.

In a particular embodiment of the invention, it may be provided for two each of the four locking elements to be formed as locking recesses 5a, and the rest as locking protrusions, whereby two locking recesses 5a each are opposite two locking protrusions by 180° in the circumferential direction. This measure allows the cap 10 to be held advantageously in a position relative to the measuring device 20 (FIG. 4), where by the jacket wall 2, in particular in the area of the intermediate section 8, is subject to elastic extension due to the small thickness $d_2$, thus allowing for particularly good adaptation of the front wall 1 to a front surface 21 (FIG. 4) of the measuring device 20 to be covered. The degree of the extension and the elasticity of the jacket wall 2 and the intermediate section 8 depend on the polymer used and the thickness $d_2$ of the jacket wall 2 in the area of the intermediate section 8.

There is additionally the possibility of providing circumferential locking elements either on the measuring device 20 or the cap 10 in the form of locking protrusions or grooves, whereby, advantageously, a circumferential locking element is only either provided on the cap 10 or the measuring device in order to allow for optimal ejection of the cap 10 from the measuring device.

In this exemplary embodiment, the entire cap 10 consists of coordinated material, specifically polymer. In this case, PETG was used, mixed with a small quantity of colourants. The use of colourants for the cap 10 allows for the distinction of different caps with different material properties, in particular different thicknesses $d_S$ of the front wall 1. However, it is also possible to make the front wall opaque or absorbent to certain wavelengths by adding colourants.

Instead of PETG (polyethylene terephthalate glycol), prior-art polymers, e.g., polyethylene or polypropylene, or mixtures thereof, may be used.

In alternative exemplary embodiments of the invention, the cap may consist of one of the following substances or a mixture thereof: PETG (Polyethylene terephthalate Glycol), PP (Polypropylene), PE (Polyethylene), PC (Polycarbonate), PVC (Polyvinyl chloride), PS (Polystyrene), ABS (Acrylonitrile butadiene styrene), HDPE (High Density Polyethylene), LDPE (Low Density Polyethylene), PET (Polyethylene terephthalate), PMMA (Polymethyl methacrylate), ECOTERM S 900 T1. In particular one or more of the following components may be added to the material of the cap 10: Additives, stabilisers, colourants, fillers, reinforcing agents, PETG/copolyester 6763.

By the specific selection of the chain length of the individual molecule chains of the polyethylene, polypropylene, or PETG, the chemical compounds to which the front wall 1 is permeable or impermeable may be determined. Thus, it is possible to measure specific samples such as blood, urine, sweat, or faeces, as well as living samples, e.g., skin, whereby only certain substances desired for the measurement can diffuse through the front wall 1, e.g., sodium, potassium, chlorine, magnesium, vitamins, hormones, glucose, alcohol, trace elements, and water vapour, whilst other components of the sample cannot diffuse, or can only diffuse after a long period of time in the range of hours through the front wall 1, e.g., water, blood, urine, or faeces. By selecting shorter chains, holes form in the respective polymer or polymer structure, such that larger molecules may diffuse through the front wall 1. The longer the chain molecules selected, the tighter the polymer structure and the smaller the molecules must be in order to penetrate the front wall 1. Additionally, the thickness $d_S$ of the front wall 1 determines permeability, because molecules can permeate a thinner front wall 1 more easily than a thicker front wall 1. To the extent that specifications on the stability of the front wall 1 require a specific thickness, alternatively, microholes or nanoholes 6 with a diameter of 0.1 nm-5 μm, or up to 400 μm, may be formed in the front wall 1, e.g., with a microneedle or laser beam.

Alternatively, chemical processes, e.g., etching, maybe used to form holes 6 in the front surface 1. In order to prevent further damage to the front surface 1, it is cleaned after forming the holes to remove the respective caustic agent, in particular rinsed.

Because the molecule size of water is 0.3 nm and the molecule size of water vapour is 0.1 nm, the provision of holes having a diameter of less than 0.3 nm can prevent the penetration of the front surface by water. Starting at a hole or pore diameter of 1 nm, water gradually comes through the front surface 1 into the inside of the hygienic cap. For measurements lasting 3 seconds, the holes or pores may also be 3-4 mm, because the water diffuses more slowly through the front surface than vapour. If a cap 10 with holes having a thickness of approximately 3-4 nm is immersed front surface 1 first into water, depending on the thickness of the front surface, it will require approximately 1 min for the front surface 1 to be penetrated.

Due to material coordination, the individual parts of the cap 10 have essentially the same properties. Special permeabilities for specific substances or radiations can only be obtained through the respective thickness $d_S$ of the front wall 1, the jacket wall 2, and the base wall 3. Thus, the front wall 1 may be made particularly thin during production so that it allows the diffusion or flow of certain materials, e.g., gases, liquids, atoms, molecules, compounds.

Figure 2:
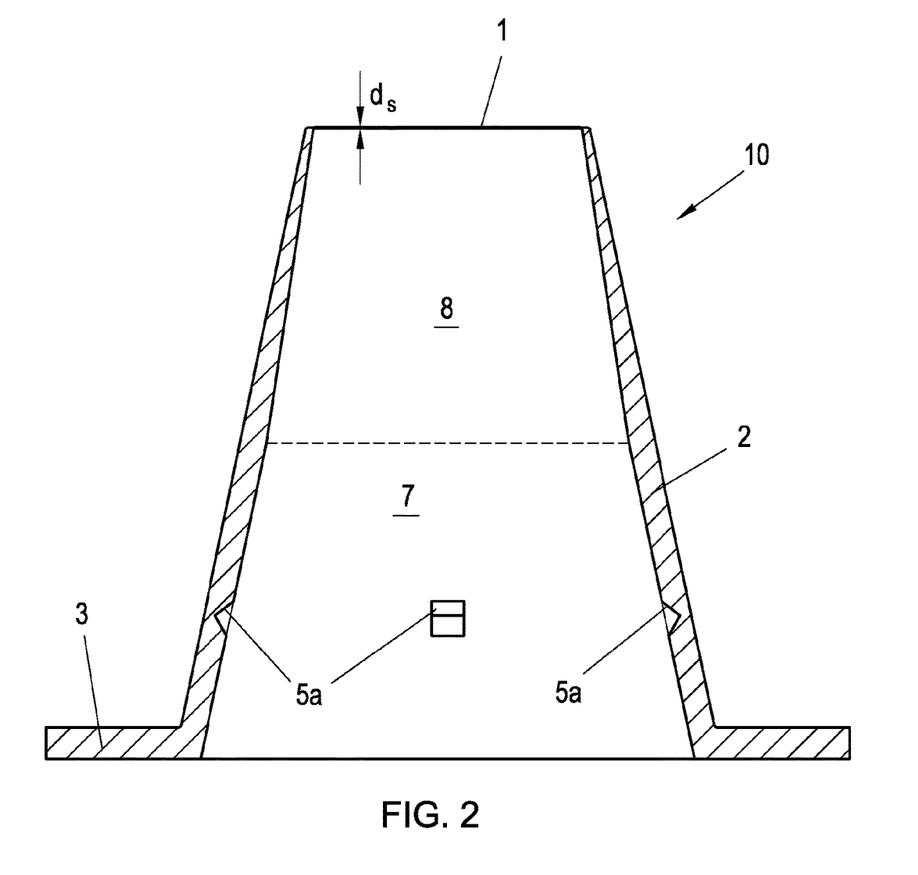
FIG. 2 shows a cross section of a cap according to a particularly simple embodiment of the invention.

The exemplary embodiment shown in FIG. 2 substantially corresponds to the exemplary embodiment shown in FIG. 1a and FIG. 1b; as such, only the differences between the two exemplary embodiments shown will be discussed in detail. The height $h_1$ of the section following from the front wall 1 corresponds approximately to the height $h_2$ of the thickening section 7 far from the front wall 1.

The jacket wall 2 is subdivided in this exemplary embodiment into two sections 7, 8, whereby both sections 7, 8 are formed circumferentially and border on one another, and a circular boundary line runs between these two sections 7, 8, the points of which each are at the same normal distance from the front wall 1. The thickness of the jacket wall 2 continuously increases from the front wall 1 in to the end of the jacket wall farthest from the front wall 1 in the axial or radial direction.

Figure 3:
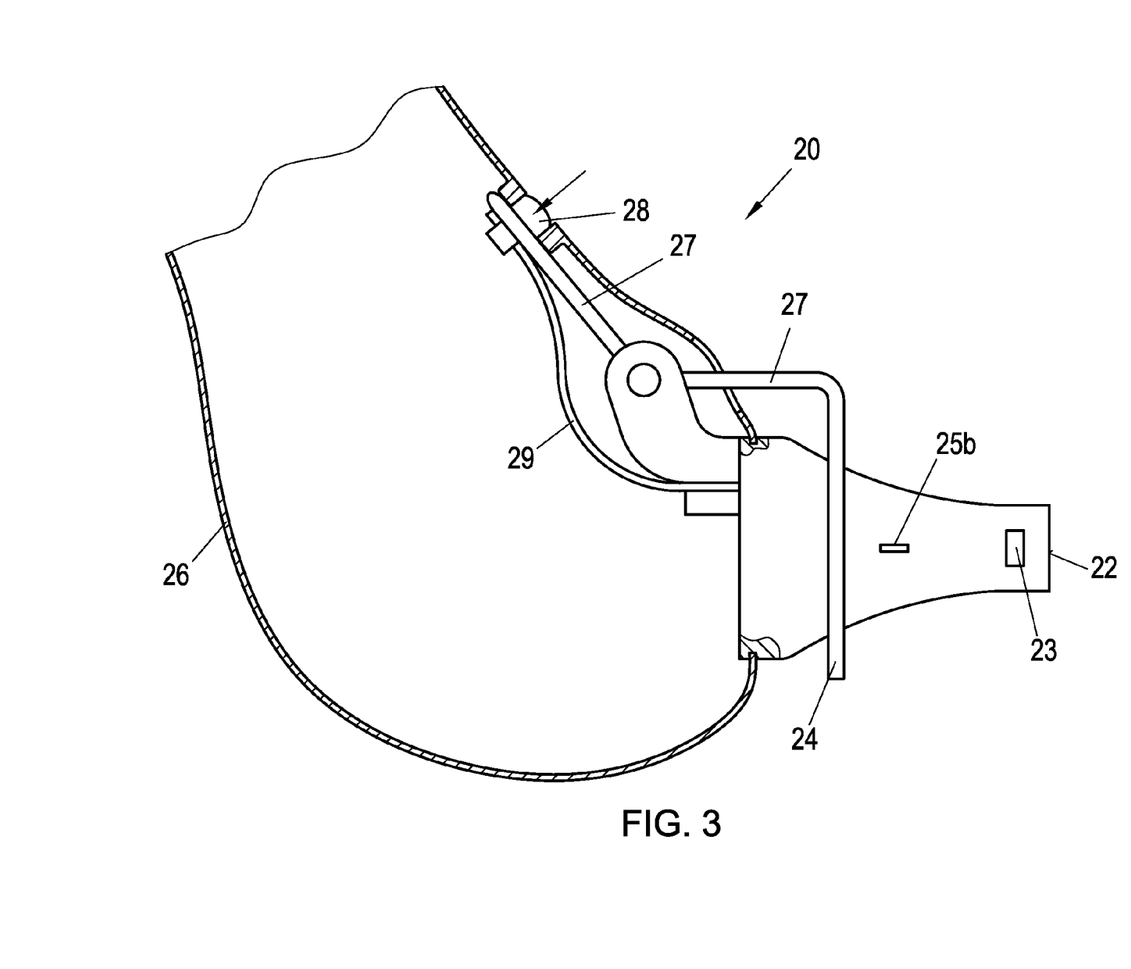
FIG. 3 shows a measuring device according to the invention.

FIG. 3 shows an embodiment of a measuring device 20 according to the invention in greater detail. This measuring device 20 has a housing 26 comprising a conically tapered component 21, which is subsequently to be covered by an aforementioned cap 10 (FIG. 4). On the end of the conically tapered component 21, a front surface 22 is arranged on or behind which a sensor 23 is located. In this exemplary embodiment, the conically tapered component 21 has an opening in the area of the front surface 22, leading to the sensor 23, such that the gases and/or substances to be measured can flow directly to the sensor 23. With a cap 10 (FIG. 4) placed on the conical component 21, the sensor 23 can be kept free of contamination.

A number of locking protrusions 25b is arranged on the conically tapered housing 21; alternatively or additionally, a number of locking protrusions may also be arranged on the lateral surface of the conically tapering component 21. As shown in FIG. 4, the cap 10 may be placed on the conically tapered component 21, such that the locking protrusions 25b protruding from the conically tapered component 21 engage with the locking recesses 5a of the cap 10. In order to attain this covered state of the measuring device 20, the cap 10 is advantageously gripped with two fingers in the lower thickening area 9 and placed or pressed onto the conically tapered component 21, such that the locking protrusions 25b of the conically tapered component 21 of the measuring device engage with the locking recesses of the jacket wall 2 of the cap 10. The cap 10 is adapted to the conically tapered component 21 such that the locking protrusions or recesses 5a, 25b are at corresponding positions, such that the cap or conically tapered component 21, when locked together, are arranged such that the front surface 1 is forced over the front wall 22, and the recess on the front surface 22 of the conically tapered component 21 in front of the sensor 23 is completely covered by the front wall 1. This is achieved, in particular, by subjecting the cap 10 in its respective section with low thickness $d_2$ to particularly substantial elastic deformation, thus generating an optimal fit for the respective measuring device or its conically tapered component 21.

The position of the locking recesses and protrusions 25b on the component 21 corresponds to the position of the locking recesses 5a and/or protrusions on the cap 10a. In particular, the locking recesses and protrusions 25b are each arranged at the same normal distance from the front surface 22 on the component 21, and advantageously evenly distributed in the circumferential direction. The total number of locking recesses and/or protrusions 25b is two in this exemplary embodiment. Alternatively, however, three, four, or more locking recesses and/or protrusions may be provided. The shape of the locking recesses or protrusions 25b is respectively adapted to the shape of the caps 10 or locking recesses 5a or protrusions of the cap 10. The locking protrusions deviate at an angle of 10-30°, no more than 1 mm, in particular no more than 0.5 mm, from the outer wall of the conically tapered component 21.

The measuring device 20 additionally has an ejection element 24, which is arranged on the end of the conically tapered component farthest from the front wall 22. This ejection element 24 is farther from the front wall 22 than the locking protrusions 25 of the conically tapered component. The ejection element 24 in this exemplary embodiment is annular, specifically cylindrically radial, and surrounds the component 21. As can be seen from FIG. 4, the base wall 3 of the cap 10 lies flat on the ejection element 24. The application of pressure to the ejection element 24 in the direction of the front wall 22 results in pressing the cap 10 out of its locked position, whereby the cap is subject to elastic deformation in the area of the locking recess 5a whilst it is being pushed out of the locked position. Due to the angled structure of the locking recess 5a and the locking protrusion 25b, the energy expended in the elastic deformation of the cap 10 is transformed into kinetic energy of the cap 10 upon leaving the locked position, thus accelerating the cap in the direction from the ejection element 24 to the front wall 21.

Figure 4A:
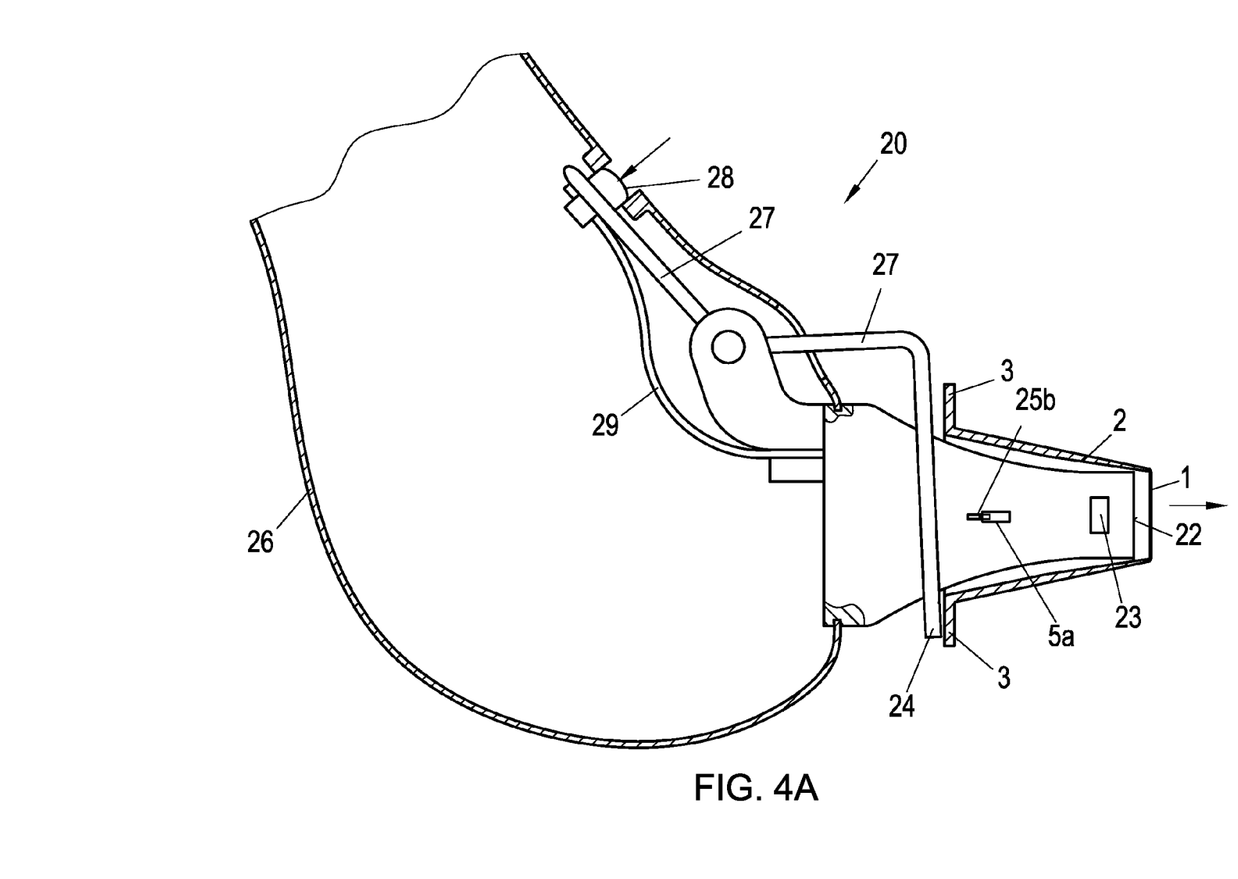
FIG. 4a shows the ejection of the cap from the measuring device.

In this exemplary embodiment, the ejection element 24 is formed in one piece with a lever extension 27. The lever extension 27 follows from the ejection element 24 of deviates from it, allowing for movement or pivoting of the ejection element 24 in the direction of the front wall 22. The lever extension 27 is pivotably connected with the housing 26 in its central area, whereby the lever extension 27 acts as a two-armed lever. On one end of this two-arm lever, the ejection element 24 is arranged; an actuator 28 in the form of a button is arranged on the other end of the two-arm lever. If the button is pressed, the end of the lever extension 27 farthest from the ejection element 24, as shown in FIG. 4a, is swiveled in an anticlockwise direction, and the ejection element 24 is pressed towards the front wall 22 due to the pivoting movement. Due to this pressure on the cap 10, the locked recesses or protrusions leave the locked position, and the cap 10 is thrown away towards the front wall 22.

By the specific articulation of the ejection element 24 due to the pivoting movement, the trajectory of the cap 10 may be set with particular precision. By the specific pivotable configuration of the ejection element 24, the combinations of locking recesses and protrusions opposite one another and corresponding to one another in this exemplary embodiment are released at different times. As a result, the cap 10 is not directly ejected, moving instead in a deviating trajectory that is directed downward and facilitates the disposal of used caps in normal handling.

Another advantageous arrangement of locking recesses or protrusions may, as discussed below, be obtained by providing only two locking recesses or protrusions at the same distance from the point at which the lever extension 27 connects to the ejection element 24 or departs from it. This ensures that the locking of the cap 10 with the measuring device 20 is released at the same time for all locked recesses and protrusions and is not delayed by re-locking of another locking protrusion in a locking recess.

Thus, caps can be ejected to the greatest possible distance from the respective measuring device 20. This has the benefit that the cap can be disposed of at a greater distance and the handling of the cap during disposal is improved by the greater ejection force, thus generally improving motivation for use and user satisfaction.

In order to prevent premature or accidental ejection or removal of a cap from the locked position on the measuring device 20, in this exemplary embodiment, a spring 29 in the form of a wire spring is provided to bias the lever extension 27, thus pushing the ejection element 24 away from the front wall 22. Only when the pressure on the actuator 28 exceeds the biasing force generated by the spring 29 will the cap 10 be ejected. In any case, this prevents accidental ejection or removal of the cap.

Alternatively, this spring 29 may also engage the part of the lever extension 27 facing the ejection element 24, or directly engage the ejection element 24 itself, pulling it away from the front wall 22.

Below, an exemplary embodiment of a method according to the invention for producing a cap 10 from a polymer film 31 is described, whereby specifically the production of the embodiment of a cap according to the invention shown in FIGS. 1a and 1b is discussed.

Figure 5:
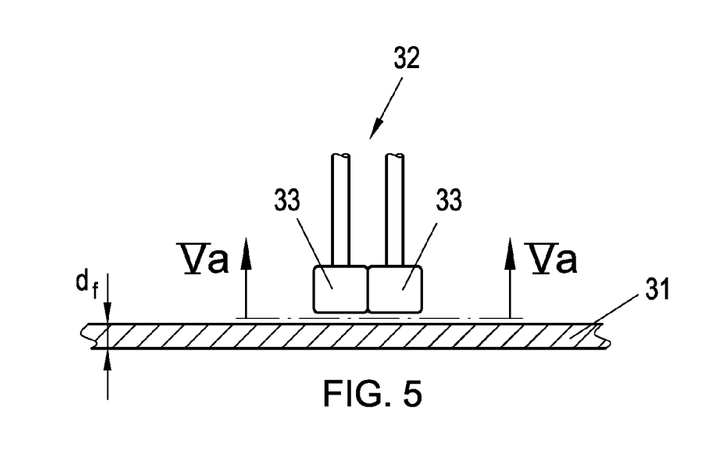
FIG. 5 shows a polymer film with which the cap is formed.

FIG. 5 shows a polymer film 31 as a raw material, with which the cap 10 is formed. The polymer film 31 originally has a thickness $d_f$ of 0.4, and consists of polyethylene terephthalate glycol (PETG).

Figure 5A:
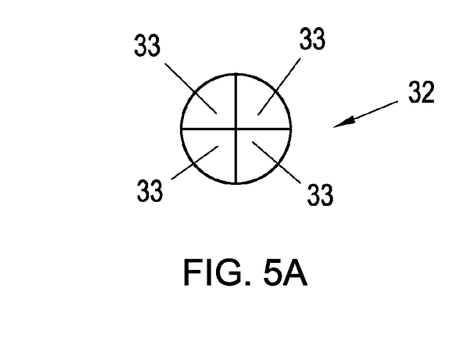
FIG. 5a shows the front surface of the stamp and its substamps.

To form a front surface 1 with a thickness $d_S$ of approximately 1 μm-10 μm, a stamp 32 comprising several substamps 33 is used. In this exemplary embodiment, the stamp 32 comprises four substamps 33. The stamp 32 is cylindrical and has a circular front surface with a radius of 1 mm. Each substamp 33 has a front surface in the form of a quarter-circle with a radius of 1 mm. All substamps 33 are arranged so as to be movable and pivotable separately from one another. FIG. 5a shows a view of the substamps 33 from the polymer film 31, as indicated by the secant Va.

Figure 6:
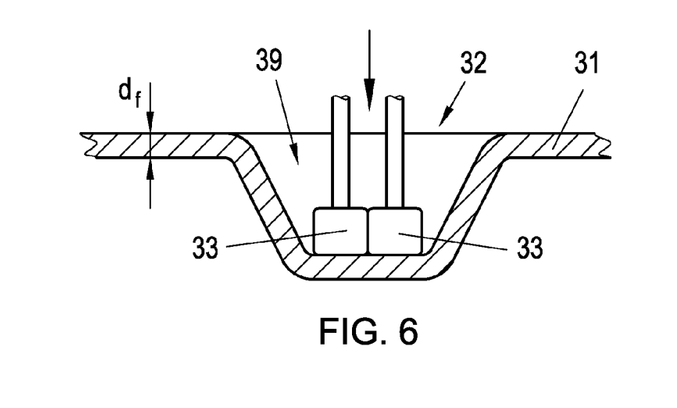
FIG. 6 shows the substamps pressing into the polymer film.

In a first moulding step, the substamps 33 abut one another, and the quadrant-shaped front surfaces of the substamps 33 together form a circular front surface. The substamps 33 are pressed forward together into the polymer film 31 in this position. As shown in FIG. 6, this deforms the polymer film 31. A volume 39 is formed that is delimited by the polymer film 31 except for the side from which the substamps 33 penetrated into the film 31. The external shape of the shape formed out of the polymer film 31 is determined by a first countermould (not shown), abutting the outer jacket wall 2 and the front wall 1 of the cap 10 formed from the film 31.

Figure 7:
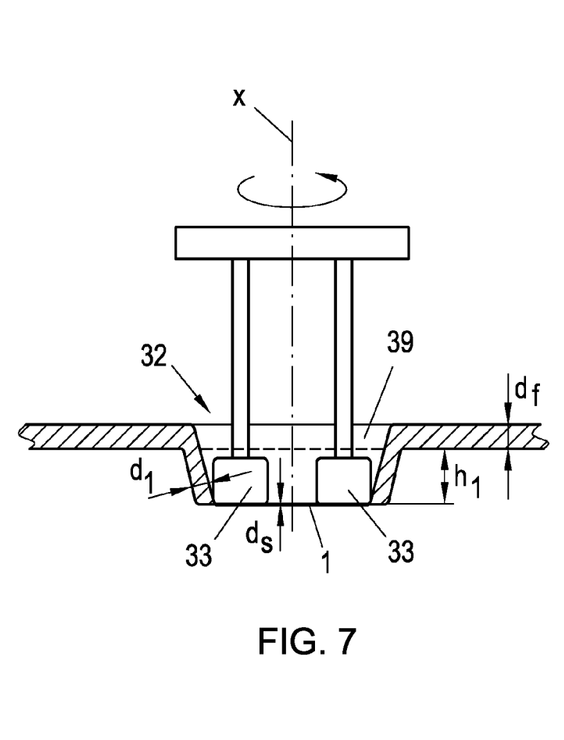
FIG. 7 shows the expansion of the substamps and the formation of the front surface of the cap.

In the next step, shown in FIG. 7, the substamps 33 are moved radially outward. In this case, the film 31 is simultaneously heated to a temperature of 40° C. in the area of the substamps 33. This causes substantial pulling and thinning of the film 31 in the intermediate area between the substamps 33, resulting in a front surface with a thickness $d_S$ of approximately 4 μm.

Generally, it is provided that the substamps 33 first move axially normal to the level of the film 31 (FIG. 6), and are only moved radially (FIG. 7) to form the front surface 1 once the substamps 33 have reached a final position in this direction.

Alternatively, of course, it is possible to combine the axial movement normal to the level of the film 31 and the radial outward displacement of the substamps 33, such that the two movements of the substamps 33 overlap.

Figure 7A:
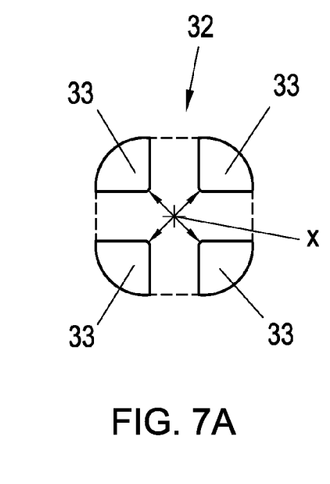
FIG. 7a shows the movement of the substamps to form a rectangular front surface.
Figure 7B:
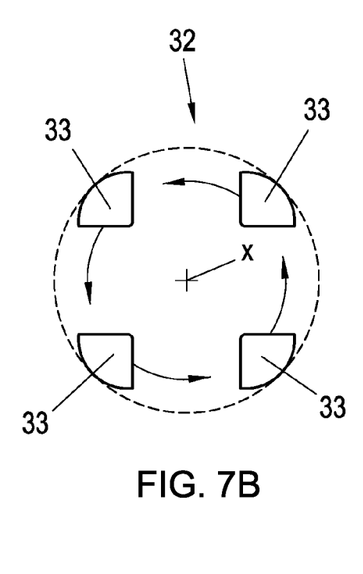
FIG. 7b shows the movement of the substamps to form a circular front surface.

To the extent that a rectangular or square front surface 1 is to be produced, it suffices for the individual substamps 33 each to be moved to a corner of the front surface 1 to be formed, as shown in FIG. 7a. However, to the extent that a circular front surface 1 is intended, the substamps 33 may additionally be displaced rotationally by the common axis X, as shown in FIG. 7b. The rotation is overlapped by the radial outward movement of the substamps 33. The individual substamps 33 thus move along a spiral path, whereby each of the cylindrical lateral surfaces of the substamps 33 is in contact with the film 31.

As noted above with regard to the formation of rectangular or square front surfaces 1, a combined axial and radial movement of the substamps 33 is also possible when forming circular front surfaces 1. In this case, the substamps 33 execute a movement along a spiral path runs helically downward and expands in spiral fashion, forming an overlap of an axial and radial movement and a rotation about the axis X.

As shown in FIG. 7, a volume 39 is formed having a height $h_1$ relative to a notional continuation of the upper edge of the film 31. This height is determined by the feed length of the individual substamps 33 axially in the direction of the axis X. The feed rate of the substamps 33 and the determination of the temperature of the substamps 33 and the film 31 in the axial direction, the thickness of the jacket wall 2 laterally delimiting the volume 39 is determined, whereby, in particular, the thickness in the area in which the polymer film 31 transitions into the jacket wall 2 is particularly dependent on the respective feed rate and temperature.

The thickness of the jacket wall 2 may be determined by the selection of the temperature of the film 31 and the substamps 33, as well as the feed rate of the substamps 33 in the axial direction. The thickness $d_1$ of the jacket wall 2 in the jacket wall section 7 formed may be continuously examined, whereby, if the thickness $d_1$ is too low, the feed rate of the substamps is reduced in the axial direction, or the temperature of the polymer film 31 or the substamps 33 is reduced. If, on the other hand, the thickness $d_1$ is too great, the feed rate of the substamps 33 in the axial direction is increased, or the temperature of the film 31 or substamps 33 is increased.

In this exemplary embodiment, a film 31 with a thickness of 0.4 mm is used that was heated to 40° C. during processing. The substamps 33 have a temperature of 45° C., and form a volume 39 with a height $h_1$ of 4 mm. Then, the substamps 33, as shown in FIG. 7a, are moved radially outward, whereby a rectangular front surface is first formed with a side length of approximately 4 mm. In another step, shown in FIG. 7b, the substamps 33 are caused to rotate, and rotate about the axis X. The cylindrically radial lateral surfaces of the substamps 33 abut the inner wall of the jacket wall formed.

Figure 8:
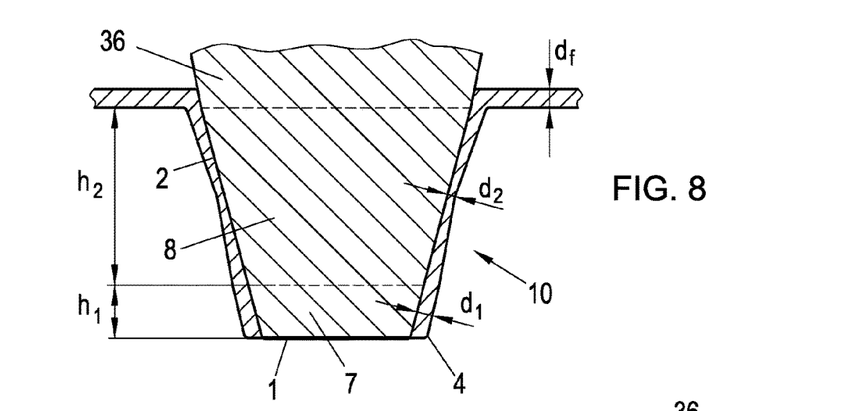
FIGS. 8 and 9 show the formation of jacket wall sections of differing thicknesses in the cap.
Figure 9:
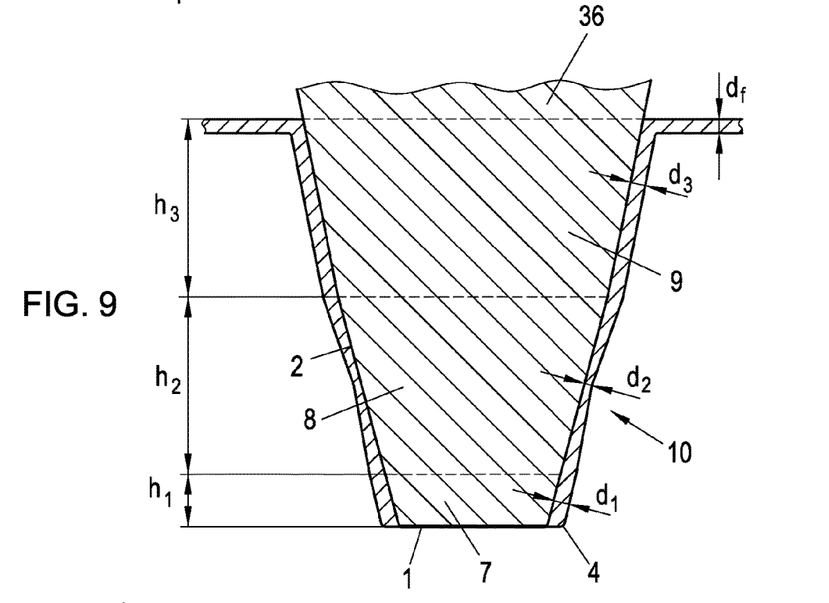

FIGS. 8 and 9 show the formation of additional jacket wall 2 sections 8, 9 of the cap with different thicknesses $d_2$, $d_3$. Instead of the substamps 33, another stamp 36, or several additional stamps, are used, the external form of which corresponds to the respective cap 10.

As shown in FIG. 8, the additional stamp 36 is pressed into the volume 39 formed, whereby the respective wall thickness $d_2$ of the area of the jacket wall 2 formed in this step ('intermediate section 8') is thinner than the wall thickness $d_1$ of the area of the jacket wall 2 ('first thickening section 7'). The thickness $d_2$ of the jacket wall 2 in the intermediate section 8, as discussed with regard to the formation of the first thickening section 7, is determined by the feed rate of the additional stamp 36 and the temperature of the polymer 31.

The external shape of the part of the cap 10 formed out of the polymer film 31, in particular the intermediate section 8, is determined by a second countermould (not shown), abutting the outer jacket wall 2 and the front wall 1 of the cap 10 formed from the film 31.

In this exemplary embodiment, the polymer film 31 remains during moulding at a temperature of approximately 40-50° C.; then, the additional stamp 36 is inserted into the second countermould. This second countermould is heated to a temperature of approximately 40-50° C. The intermediate area between the additional stamp 36 and the second countermould corresponds to the desired shape of the cap 10 in the first thickening section 7 and the intermediate section 8; in this exemplary embodiment, the wall thickness in the intermediate section 8 is less than in the first thickening section 7.

Then, as shown in FIG. 9, the additional stamp 36 is moved further forward, whereby a second thickening section 9 is formed, the thickness $d_3$ of which is greater than the thickness $d_2$ in the intermediate section.

The external shape of the section of the cap 10 formed out of the polymer film 31, in particular the second thickening section 9 following from the intermediate section 8, is determined by a third countermould (not shown), abutting the outer jacket wall 2 and the front wall 1 of the cap 10 formed from the film 31.

In this exemplary embodiment, the polymer film 31 remains during moulding at a temperature of approximately 40-50° C.; then, the additional stamp 36 is inserted into the second countermould. The third countermould is heated to a temperature of approximately 40-50° C. The intermediate area between the additional stamp 36 and the third countermould corresponds to the desired shape of the cap 10 in the first thickening section 7, the intermediate section 8, and the second thickening section.

Figure 10:
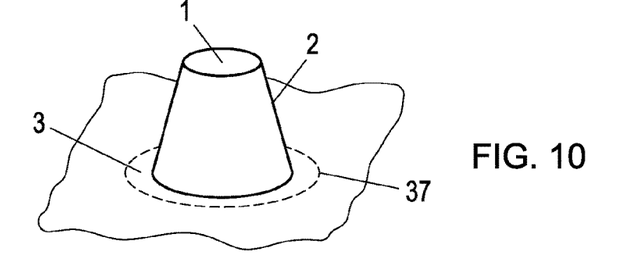
FIG. 10 shows the finishing of the cap by separating it from the polymer film.

FIG. 10 shows the finishing of the cap by separating it from the polymer film. After the forming and contouring of the entire jacket wall 2, the jacket wall remains connected to the film 31. In a final step, the film 31 is separated along a specified cutting line 37; in this exemplary embodiment, the polymer film 31 is punched out along the jacket wall. This separates the cap 10 from the rest of the polymer film 31.

In this exemplary embodiment, the cutting line 37 runs circularly and coaxially along the hollow frustoconical lateral surface 2. By cutting along the cutting line 37, a base wall 3 of the cap 10 is formed that runs parallel to the front surface and radially outward from the end of the lateral surface 2 farthest from the front surface 1. Alternatively, it is also possible to form the base wall 3 facing away from the front wall 1 and deviating radially outward from the lateral surface 2 at an angle of up to 20°, in particular up to 10°, by means of an additional deformation process.

After the conclusion of the moulding process, either before or after cutting the cap 10 along the cutting line 37, the polymer film 31 forming the cap 10 is heated for a specified period of 3-4 s to a temperature between 50 and 120° C. depending on the polymer used, in this case to 75° C. Over this process, the polymer forming the polymer film 31 is reshaped by the heating. The polymer film 31 loses its thermoplastic properties. By the action of heat, the molecule chains forming the polymer film 31 are split, resulting in greater permeability of the cap 10, in particular in the area of the front surface 1. The longer the heat acts on the polymer film 31, and the greater its intensity, the shorter the molecule chains forming the film 31 and the greater the permeability of the front surface 1 will be.

Alternatively, instead of heating the cap, holes 6 may be formed, in this case microholes or nanoholes, preferably exclusively in the front wall 1, in order to obtain a greater permeability for molecules of a particular size. The micro- and nanoholes can be formed using a laser beam or by perforation with a heated microneedle.

It is particularly advantageous if the cap 10 is particularly rigid in the area farthest from the circumferential edge 4, which serves to stabilise the cap. The rigidity of the cap 10 increases towards the centre of the jacket wall 2, whereby the jacket wall 2 is more rigid in the area surrounding the front wall 1. The elasticity of the jacket wall 4 is greatest in the area of its thinnest point or least rigid point.

Preferably, the stiffness or elasticity of the jacket wall 4 is homogeneously distributed over the circumference, varying only with the distance from the front wall 1.

The invention claimed is:

1. A cap, comprising:
  a front wall delimited by a circumferential edge and being gas-permeable; and
  a jacket wall attached to said circumferential edge of said front wall, at least part of the cap having a first thickness that is less than a second thickness of said jacket wall in a section of said jacket wall in an area or end of said jacket wall facing away from said front wall;
  said jacket wall in an area near said front wall, having a first thickening section following from the circumferential edge, in which a thickness of said jacket wall exceeds a thickness of said front wall;
    said jacket wall having an intermediate section following from said first thickening section, said first thickness of said jacket wall in said intermediate section being less than said thickness of said jacket wall in said first thickening section;
    said jacket wall having a second thickening section, following from said intermediate section and extending until an end of said jacket wall that is farthest from said front wall; and
    said second thickness of said jacket wall being greater in said second thickening section than said first thickness of said jacket wall in said intermediate section;
  said jacket wall having a thickness being a continuous course free of kinks or edges in an axial or radial direction; and/or
    a respective average thickness in respective one of said first thickening section, said second thickening section and said intermediate section of said jacket wall being deemed to be said thickness; and/or
    said jacket wall, with an exception of an area of said locking protrusions or said recesses, being rotationally symmetric;
  said thickness of said first thickening section, said first thickness of said intermediate section, and said second thickness of said second thickening section having the following ratio:
  2<d1:d2<5 and/or 2<d3:d2<5 and/or 0.8<d1:d3<1.25;
  d1 being said thickness of said first thickening section, d2 being said first thickness of said intermediate section, and d3 being said second thickness of said second thickening section; and/or
    said thickness of said first thickening section, said first thickness of said intermediate section, and said second thickness of said second thickening section being set as follows:
  150 μm<d1 <250 μm and/or 50 μm<d2<100 μm and/or 150 μm<d3<250 μm;
  a height h1 of said first thickening section, a height h2 of said intermediate section, and a height h3 of said second thickening section having the following ratio:
  0.2<h1:h2<0.6 and/or 0.8<h3:h2<1.25 and/or 0.2<h1:h3<0.6; and/or
    said jacket wall having a height of 2-80 mm; and/or
    a ratio between said height and a maximum dimension, being a diameter or diagonal, of said front wall is between 0.01 and 55;
  said front wall being circular and having a diameter of 1-50 mm; or
    said front wall being square or rectangular, and side edges of said front wall having a length between 2 and 40 mm;
  said cap having at least one of locking recesses formed therein or locking protrusions on said end of said jacket wall facing away from said front wall for removable attachment to a measuring device; or
  at least one of said locking recesses or said locking protrusions each having at least one of a same normal distance from said front wall, are distributed evenly in a circumferential direction of said jacket wall, or whereby a total number of said locking recesses and/or said locking protrusions being two or four; and/or
  at least one of said locking recesses or said locking protrusions protruding away from said jacket wall at an angle of 5°-40° and/or no more than 2 mm.

2. The cap according to claim 1, wherein said jacket wall has at least one circumferential section, said first thickness is in said at least one circumferential section.

3. The cap according to claim 1, wherein:
  said front wall, at at least one point, has a thickness less than 100 μm; and
  said front wall has a constant thickness over its course.

4. The cap according to claim 1, further comprising a base wall continuing from said jacket wall on said end facing away from said front wall and running outward from said jacket wall parallel or at an angle of no more than 10° to said front wall, said base wall formed with a shape of a circular ring and has at least one of an outer radius between 2 mm and 50 mm, an inner radius between 1 mm and 45 mm, or a circular ring width from 0.5 to 35 mm.

5. The cap according to claim 1, wherein said jacket wall in an area of said circumferential edge of said front wall protrudes outward at an angle of 20°-95° to said front wall, whereby said jacket wall expands conically.

6. The cap according to claim 1, wherein:
  said front wall is penetrable by at least one of radiation, vapor, moisture, particles, or light; and/or
  said front wall has a number of microholes formed therein and selected from the group consisting of vapor-permeable microholes and gas-permeable microholes.

7. The cap according to claim 1, wherein:
  said front wall and said jacket wall are formed as one of coordinated parts or as a single piece unit, at least one of said front wall and said jacket wall formed of at least one material selected from the group consisting of a thermoplastic, a plastically deformed polymer, a deformable polymer, polyethylene terephthalate glycol (PETG), polypropylene (PP), polyethylene (PE), polycarbonate (PC), polyvinyl chloride (PVC), polystyrene (PS), acrylonitrile butadiene styrene (ABS), high density polyethylene (HDPE), low density polyethylene (LOPE), polyethylene terephthalate (PET), polymethyl methacrylate (PMMA), ECOTERM S 900 T1, and PETG/Copolyester 67639;
  said front wall and said jacket wall further containing at least one further material selected from the group consisting of additives, stabilisers, colorants, fillers and reinforcing materials;
  said front wall is opaque or absorbent to visible wavelengths.

* * * * *